US 6,699,291 B1

(12) United States Patent
Augoyard et al.

(10) Patent No.: US 6,699,291 B1
(45) Date of Patent: Mar. 2, 2004

(54) ANTERO-POSTERO-STABILIZED KNEE PROSTHESIS

(75) Inventors: Marc Augoyard, Tassin la Demi Lune; Gerard Bascoulergue, deceased, late of Le Touquet, by Limon Bascoulergue, Benjamin Bascoulerque, Maud Bascoulerque, legal representatives; Maurice Basso, Hyeres; Rene Bertocchi, Lyons; Philippe Charret, Fontaine sur Saone; Philippe Courcelles, deceased, late of Dardilly, by Celine Courcelles, Julien Courcelles, Marie Auuick Courcelles, legal representatives; Jean-Louis Debiesse, Vienne; Laurent Dupre La Tour, Letrat; Guy Eyraud, Ville Sous Anjou; Jean-Philippe Fayard, Saint Just Saint Rambert; Paul-Henri Hulin, Auxerre; Francois Lecuire, Hyeres; Gilles Melere, Annecy; Joseph Millon, La Ravoire; Jean-Paul Passot, St Genest Lerpt; Jacques Peyrot, Tassin la Demi Lune; Marc Relave, Andrezieux Boutheon; Gerard de Witte, Chateauneuf sur Isere; Michel Vernizeau, Valence, all of (FR)

(73) Assignee: Merck Biomaterial France, Valence Cedex (FR)

( * ) Notice: Subject to any disclaimer, the term of this patent is extended or adjusted under 35 U.S.C. 154(b) by 0 days.

(21) Appl. No.: 09/539,883

(22) Filed: Mar. 31, 2000

(30) Foreign Application Priority Data

Apr. 1, 1999 (FR) .............................................. 99 04286

(51) Int. Cl.$^7$ ................................................. A61F 2/38

(52) U.S. Cl. ............................... 623/20.27; 623/20.24; 623/20.31

(58) Field of Search .......................... 623/20.21, 20.24, 623/20.27, 20.31

(56) References Cited

U.S. PATENT DOCUMENTS

| 4,959,071 | A | * | 9/1990 | Brown | 623/20.27 |
|---|---|---|---|---|---|
| 5,007,933 | A | * | 4/1991 | Sidebotham | 623/20.27 |
| 5,011,496 | A | * | 4/1991 | Forte | 623/20.27 |
| 5,271,747 | A | * | 12/1993 | Wagner | 623/20.27 |
| 5,282,869 | A | * | 2/1994 | Miyajima | 623/20.27 |
| 5,330,532 | A | * | 7/1994 | Ranawat | 623/20.27 |
| 5,358,527 | A | * | 10/1994 | Forte | 623/20.27 |
| 5,800,552 | A | * | 9/1998 | Forte | 623/20.27 |
| 6,162,254 | A | * | 12/2000 | Timoteo | 623/20.33 |
| 6,203,576 | B1 | * | 3/2001 | Afriat | 623/20.27 |
| 6,206,926 | B1 | * | 3/2001 | Pappas | 623/20.27 |
| 6,201,445 | B1 | * | 4/2001 | Zawadzki | 623/20.33 |

FOREIGN PATENT DOCUMENTS

| EP | 0749734 | 12/1996 |
|---|---|---|
| FR | 2718952 | 10/1995 |

* cited by examiner

Primary Examiner—Michael J. Milano
(74) Attorney, Agent, or Firm—Dennison, Scheiner & Schultz

(57) ABSTRACT

A prosthesis, such as a knee prosthesis, for the lower limb including a femur prosthetic element having a block presenting a lug running into the trochlea and adjacent to a notch from which a convex bearing surface extends, and a tibia prosthetic element having an insert with a sagittally oriented elevation defining a projection for antero-postero stabilization engaged in the notch when the prosthesis is in the extended position and which runs into a concave sliding ramp that extends to the rear edge of the insert.

11 Claims, 5 Drawing Sheets

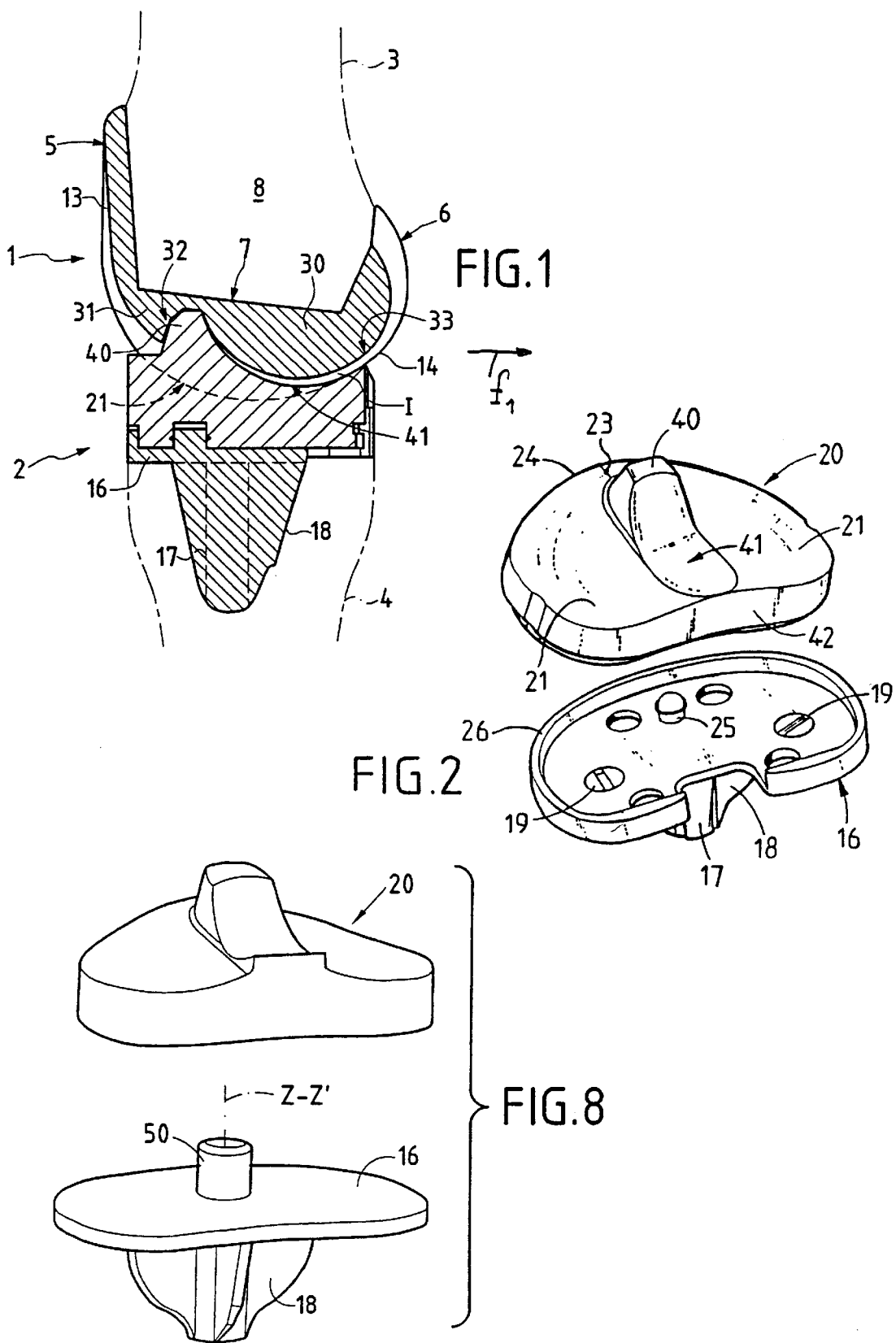

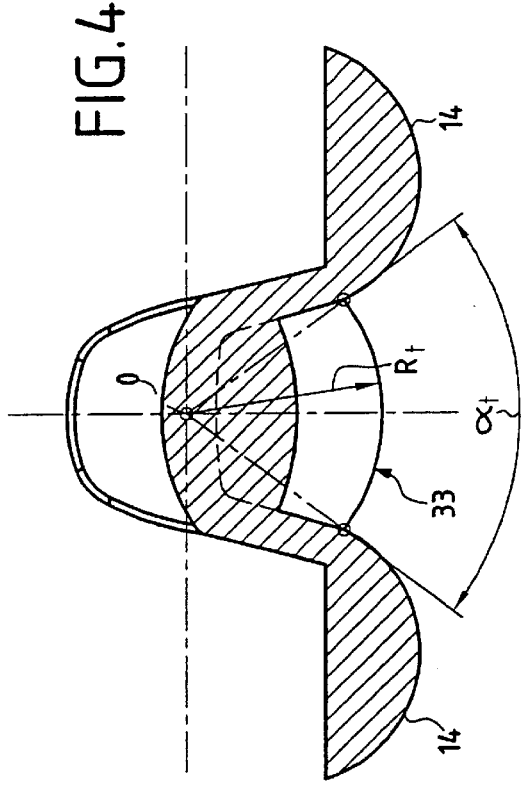
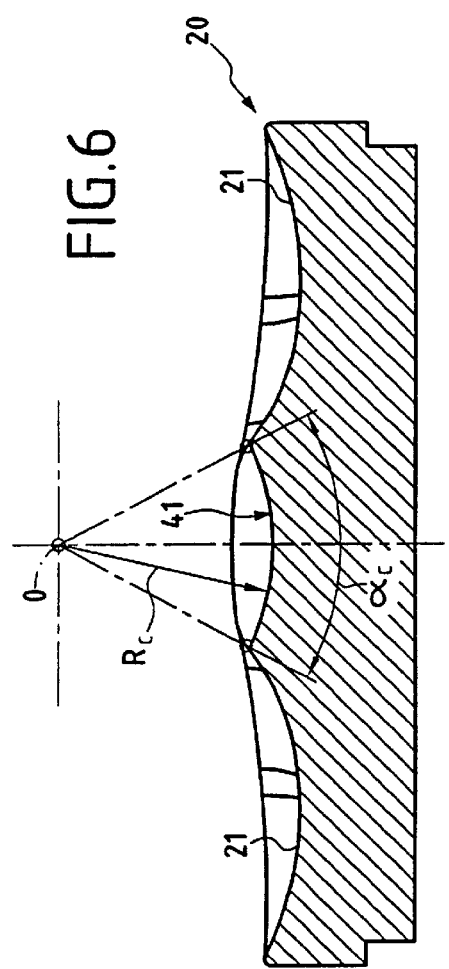
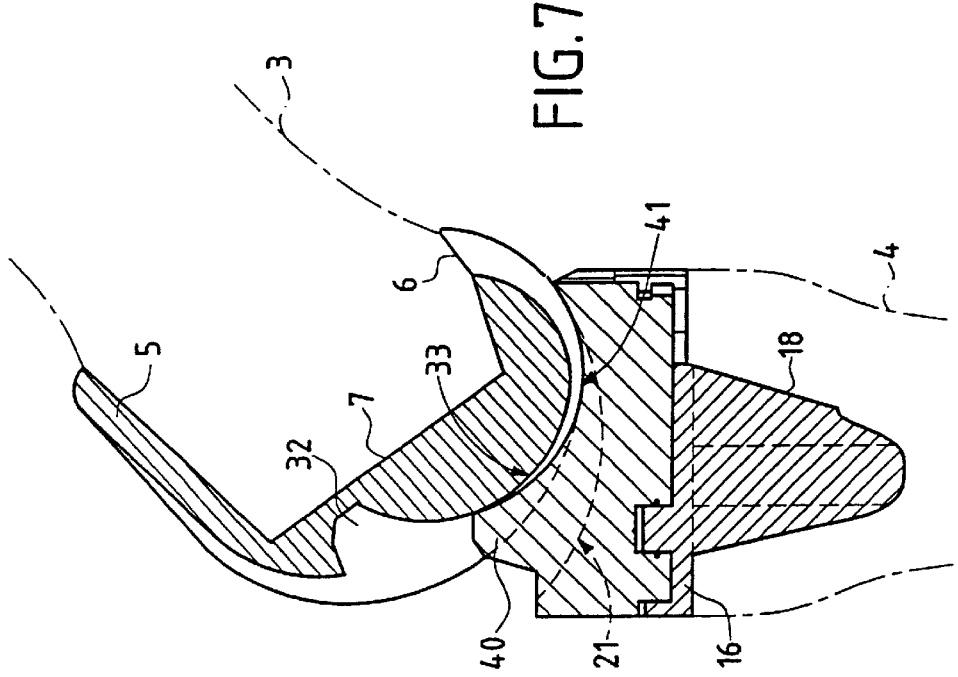

ANTERO-POSTERO-STABILIZED KNEE PROSTHESIS

The present invention relates to joint prostheses, and more particularly it relates to the field of knee prostheses.

BACKGROUND OF THE INVENTION

The term "knee prosthesis" applies to artificial joint systems intended to replace the natural joint constituted by the conformation of the bottom epiphysis of the femur, by the conformation of the complementary top epiphysis of the tibia, and also by the femoro-patellar element.

In the prior art, a large number of proposals have been made that apply to the above technical field.

Total prostheses have thus been proposed that are said to be "linked" in that they make use of two complementary parts which are united by a physical hinge system, such as at least one pin, constituting the artificial pivot system enabling the knee to bend in a direction that is perpendicular to the sagittal or antero-posterior plane.

Prostheses have also been proposed that are said to be "free" which are constituted, unlike the above prostheses, on the basis of two elements for fitting respectively to the bottom epiphysis of the femur and to the top epiphysis of the tibia for the purpose of co-operating by relative sliding while being maintained in surface contact in particular via natural internal and external lateral ligaments, and without making use of any physical hinge link between the two elements.

In reality, prostheses whether "linked" or "free" are designed to satisfy a specific joint-restoration requirement corresponding to a joint problem that needs to be overcome or compensated.

That is why a very large number of technical solutions have been proposed, each setting out to resolve a specific joint problem.

Such prostheses must certainly be considered as having provided solutions that are practical, suitable, and acceptable.

However, with the hindsight now available to practitioners, it can be considered that the prostheses that are presently proposed, and more particularly those of the free type, do not make it possible to maintain antero-posterior stabilization, nor to maintain the relative rearward displacement or sliding of the bottom epiphysis of the femur relative to the top epiphysis of the tibia during flexing, which displacement is known as "rollback", while nevertheless making partial rotation possible as allowed by the natural knee joint.

However, it is becoming ever more clear that these requirements correspond to anatomical needs which it is important to maintain when prosthetically restoring a joint, at least for the purpose of reducing the ligament fatigue that such prostheses can cause.

OBJECT AND SUMMARY OF THE INVENTION

The object of the invention is to satisfy that requirement by proposing a novel total knee prosthesis in the form of a single unit which is characterized by implementing complementary technical means between the femur prosthetic element and the tibia prosthetic element, which complementary technical means are designed to perform their own functions without interfering with the basic functional relationship between the condyles of the femur element and the glenoid cavities of the tibia element.

The total knee prosthesis of the invention is of the type comprising:

- a U-shaped femur prosthetic element defining a housing for engaging the resectioned epiphysial portion of a femur and having an anterior portion defining a trochlea by its front face and a distalo-posterior portion defining two condyles; and
- a tibia prosthetic element comprising a base for fitting to the resectioned epiphysial portion of a tibia and an insert mounted on the base and presenting, facing the femur prosthetic element, two glenoid cavities for co-operating with the condyles;

wherein:

- the femur prosthetic element includes, between the condyles, a block presenting, in its outside face relative to the housing, a lug connecting to the trochlea and adjacent to a notch from which a convex bearing surface extends as far as the end portion of the block; and
- the insert and the tibia prosthetic element include a sagittally-oriented elevation between the glenoid cavities and defining, relative to the front edge of said insert, an antero-posterior stabilization projection that is engaged in the notch when the prosthesis is in the extended position and that is connected to a concave sliding ramp extending as far as the rear edge of the insert to co-operate with the facing convex bearing surface when the prosthesis is in the extended position so as to define a gap of section that increases from the zone where the projection engages in the notch, all the way to said rear edge.

BRIEF DESCRIPTION OF THE DRAWINGS

Various other characteristics appear from the following description given with reference to the accompanying drawings which show embodiments of the invention as non-limiting examples.

FIG. 1 is a section in elevation substantially on the sagittal plane of a prosthesis shown implanted between the femur and the tibia of a subject.

FIG. 2 is a perspective view showing a component element of the prosthesis.

FIG. 4 is a cross-section on line IV—IV of FIG. 3.

FIG. 6 is a cross-section on line VI—VI of FIG. 5.

FIG. 7 is a section analogous to FIG. 1, showing the prosthesis in a different functional position.

FIG. 8 is a perspective view showing a variant embodiment.

MORE DETAILED DESCRIPTION

Figure 3:
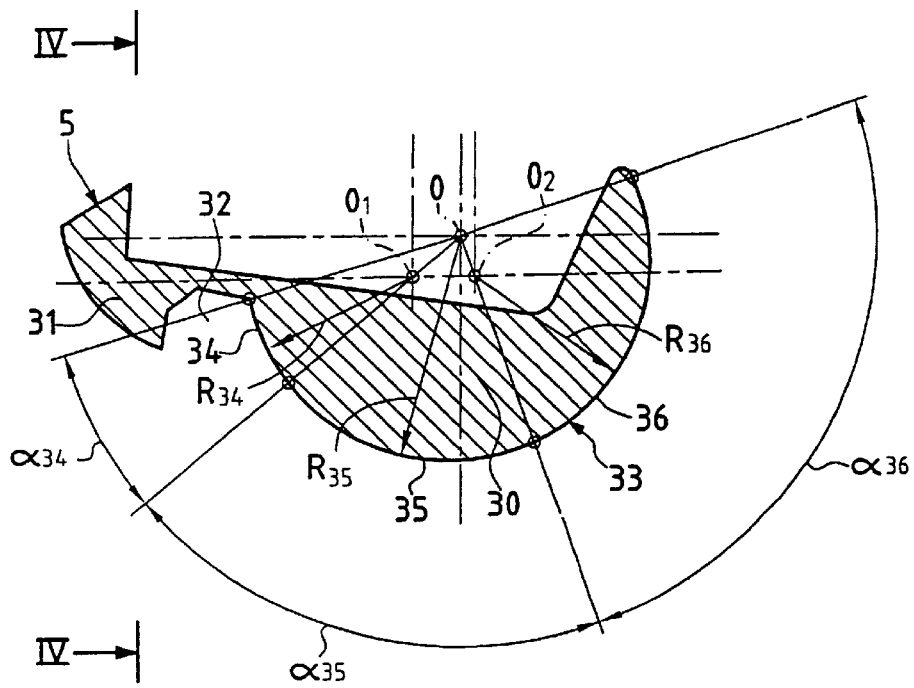
FIG. 3 is a section in the sagittal plane and on a larger scale, showing a structural characteristic of an embodiment of the femur prosthetic element.

FIG. 1 shows the prosthesis of the invention constituted by a femur prosthetic element 1 and by a tibia prosthetic element 2 for fitting respectively on the bottom epiphysis of the femur 3 and on the top epiphysis of the tibia 4, after resection of the bone.

The femur element 1, which can be made of any suitable material known to the person skilled in the art, is substantially U-shaped in a sagittal plane, comprising a front or anterior portion or branch 5, a rear or posterior portion or branch 6 that is generally shorter than the branch 5, and a core 7 linking the branches together.

The inside surface defined by the femur element defines a kind of polygonal housing 8 for receiving the epiphysis 3 that has previously been subjected to complementary resection.

The femur element is shaped so that the outside surface of its large branch 5 presents a patellar surface 13 defining in conventional manner a trochlea suitable for co-operating with the natural protuberance or with an artificial button presented or carried by the patella (not shown).

The outside surface of the femur element 1 corresponding to the core 7 and to the branch 6 presents two condyles 14 which define a distal portion and a posterior portion.

As such, the condyles 14 should be considered as forming part of the prior art and as being well understood by the person skilled in the art.

The condyles 14 are for co-operating via their distal and posterior portions with the tibia prosthetic element which, in accordance with the invention, comprises a base 16 whose bottom face is provided with at least one tang 17 optionally reinforced by gussets 18. The tang 17 is designed to be implanted in the tibial epiphysis 4 with or without a bonding cement. As is known, the fixing of the base 16 can also make use of screws 19 (FIG. 2).

The tibial base serves to support an insert 20 which is preferably made of a suitable plastics material such as polyethylene. The insert 20 is shaped so that it presents two glenoid cavities 21 for co-operating with the outer surfaces of the condyles 14, and a spike 23 formed in the sagittal portion from the anterior edge 24 and between the glenoid cavities 21.

In the example shown in FIG. 2, the insert 20 is mounted on the base 16 by being centered on a peg 25 and by being engaged inside a rim 26.

A tibia prosthetic element shaped as described above should be considered, in the general sense, as being part of the prior art known to the skilled person.

In the invention, the femur prosthetic element 1 is made so as to include in its inter-condyle portion, a block 30 which is shaped so that its outer surface, relative to the housing 8, is set back relative to the outer surfaces of the condyles 14. This setback surface is arranged, in its portion linking with the branch 5, to form a lug 31 which defines a kind of notch 32 from which there extends a bearing surface 33 terminating at the extreme rear portion of the branch 6.

In the embodiment of FIGS. 3 and 4, the bearing surface 33 is of pseudo-spherical shape defined by an anterior surface portion 34 beginning from the bottom of the notch 32. This surface portion is defined by a radius $R_{34}$ of center $O_1$ situated before and beneath a reference center O for the anterior branch 5. The radius $R_{34}$ occupies an angular extent $a_{34}$.

The bearing surface or ramp 33 is also defined by a surface portion 35 following the portion 34 and characterized by a radius $R_{35}$ of center O and occupying an angular extent $a_{35}$.

The frustoconical bearing surface 33 is also defined by a third surface portion 36 of radius $R_{36}$, of center $O_2$ situated beyond and beneath the reference center O relative to the anterior portion 5. The radius $R_{36}$ occupies an angular extent $a_{36}$.

In addition, the surface 33 is characterized by a transverse radius of curvature $R_t$, of center O, and occupying an angular extent $a_t$. This transverse radius of curvature $R_t$ is constant for the entire ramp 33, from the beginning of the surface portion 34 in the bottom of the notch 32.

Figure 5:
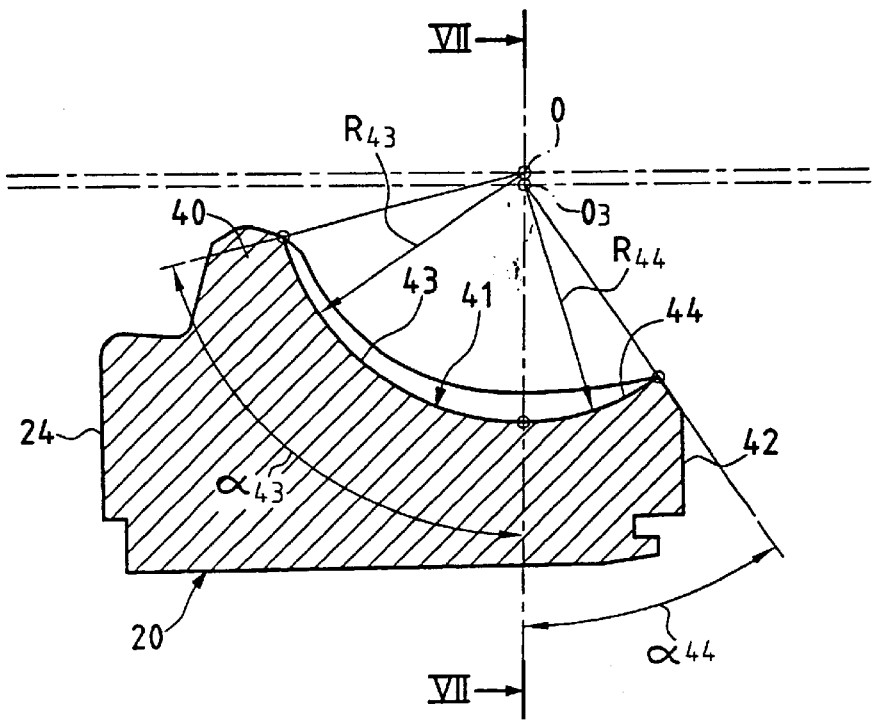
FIG. 5 is a section analogous to FIG. 3, but relating to the tibia prosthetic element complementary to the femur element of FIG. 3.

In complementary manner, in this embodiment, the tibia prosthetic element, as shown in FIGS. 5 and 6, comprises, from the insert 20 and along the spike 23, a projection 40 of shape that is complementary to the notch 32, the projection being set back from the anterior edge 24 and being connected to a ramp 41 which extends along the sagittal axis towards the posterior edge 42 of the insert 20. The "sliding" ramp 41 is generally concave in shape and is characterized by a first surface portion 43 that is spherical, of radius $R_{43}$, of center O, and occupying an angular extent $a_{43}$. The ramp 41 also comprises a second surface portion 44 that is spherical, of radius $R_{44}$, of center $O_3$ situated vertically beneath the center O, and occupying an angular extent $a_{44}$.

The surface 41 is also characterized in the sagittal plane by a radius of curvature $R_c$ of center O and occupying an angular extent $a_c$ of about 57.50°, as can be seen in FIG. 6.

Co-operation between the facing surfaces of the prosthetic elements 1 and 2, i.e. the notch 32, the ramp 33, the projection 40, and the ramp 41, leads to a relative position in the extended state as shown in FIG. 1 in which the projection 40 is fully engaged in the notch 32 with surface co-operation between the lug 31 and the surface portion 34, while simultaneously the condyles 14 are co-operating with the glenoid cavities 21.

In this state, the bearing surface 33 and the ramp 41 between them define a gap I extending from the notch 32 and of section that increases from said notch towards the posterior portion or branch 6.

As can be seen in FIG. 1, in such a relative position, co-operation between the projection 40 and the notch 32 produces antero-posterior stabilization that is effective without any risk of sliding in the sagittal plane.

FIG. 7 shows a partially flexed state in which co-operation between the facing surfaces takes place between the prosthetic elements 1 and 2 firstly by sliding between the condyles 14 and the glenoid cavities 21, and secondly by relative sliding between the bearing surface 33 and the ramp 41.

In this position, the prosthetic elements 1 and 2 are suitably guided in co-operation and, by the action of the bearing surface 33 behaving like a cam co-operating with the ramp 41, they reproduce the natural rearward relative movement or displacement known as "rollback" between the femur and the tibia, as shown by arrow $f_1$.

It should be observed that in the co-operation between the prosthetic elements as described above, the possibility of partial rotation is maintained because of the co-operation between the surfaces of a pseudo-spherical nature that constitute the convex bearing surface 33 and the concave ramp 41.

As an indication, Table I below gives the ranges of numerical values given to the lengths and the angular extents for the various radii of the bearing surface 33 for a set of six sizes of prosthesis.

TABLE I

|     | $R_{34}$ in mm | $R_{35}$ in mm | $R_{36}$ in mm | $R_t$ in mm | $a_{33}$ in ° | $a_{34}$ in ° | $a_{35}$ in ° | $a_t$ in ° |
|-----|------|------|------|----|-------|----|-------|-------|
| min | 12.4 | 17.7 | 14.6 | 14 | 20.81 | 70 | 89.05 | 70.64 |
| max | 17   | 24.4 | 20.1 | 18 | 22.75 | 70 | 91.67 | 80.87 |

As an indication, Table II below gives the ranges of numerical values given to the lengths and the angular extents of the various radii of the ramp 41 for the same set of six sizes of prosthesis.

TABLE II

|     | $R_{43}$ in mm | $R_{44}$ in mm | $R_c$ in mm | $a_{43}$ in ° | $a_{44}$ in ° | $a_c$ In ° |
|-----|-------|------|----|-------|-------|-------|
| min | 17.77 | 16.5 | 15 | 75.51 | 35.54 | 57.42 |
| max | 24.4  | 20.5 | 20 | 76.31 | 40.02 | 64.72 |

A variant embodiment is shown in FIG. 8 which shows that the insert 20 can be mounted on the base 16 via a rotary pivot 50 projecting up from the flat surface thereof along a vertical axis Z-Z'. Under such circumstances, the base 16 does not have a rim 26, thereby allowing the insert 20 to pivot to some extent in either direction about the axis Z-Z'.

Such an assembly can be provided to favor partial rotation, as mentioned above, in which case the prosthetic elements 1 and 2 can then have co-operating surfaces which, instead of being pseudo-spherical, can be thought of as being surfaces that are pseudo-cylindrical.

Figure 9:
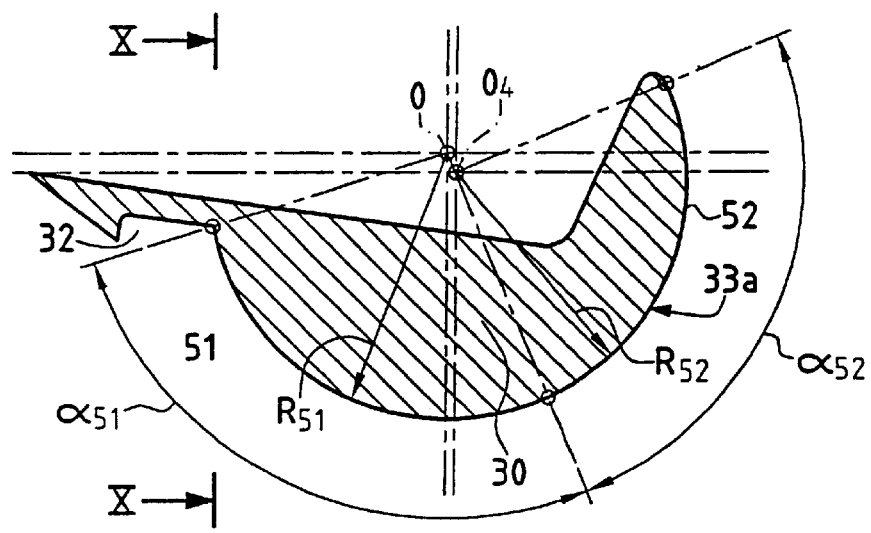
FIG. 9 is a section on a larger scale showing the femur prosthetic element of this variant.
Figure 11:
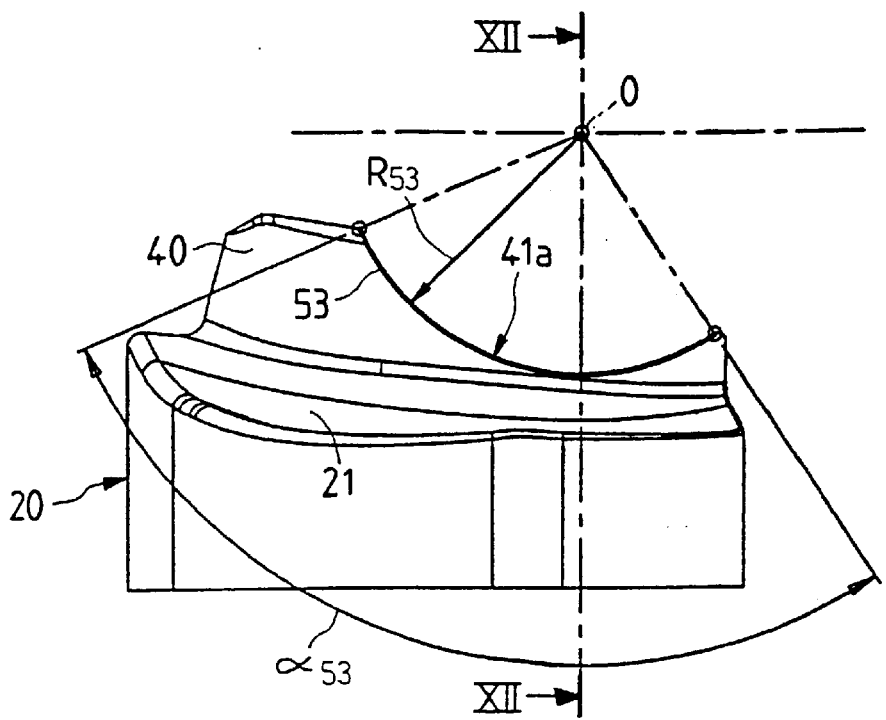
FIG. 11 is an elevation view of the tibia prosthetic element corresponding to the femur element of FIG. 9.

FIG. 9 shows that in such an embodiment, the bearing surface 33a is then constituted, starting from the notch 32, by a surface portion 51 that is cylindrical, of radius $R_{51}$, of center O, and occupying an angular extent $a_{51}$. The bearing surface 33a is also defined by a second wall portion 52 that is cylindrical, that extends from the portion 51, and that is defined by a radius $R_{52}$ of center $O_4$ situated beneath and beyond the reference center O relative to the anterior branch of the prosthetic element 1. The radius $R_{52}$ occupies an angular extent $a_{52}$.

Figure 10:
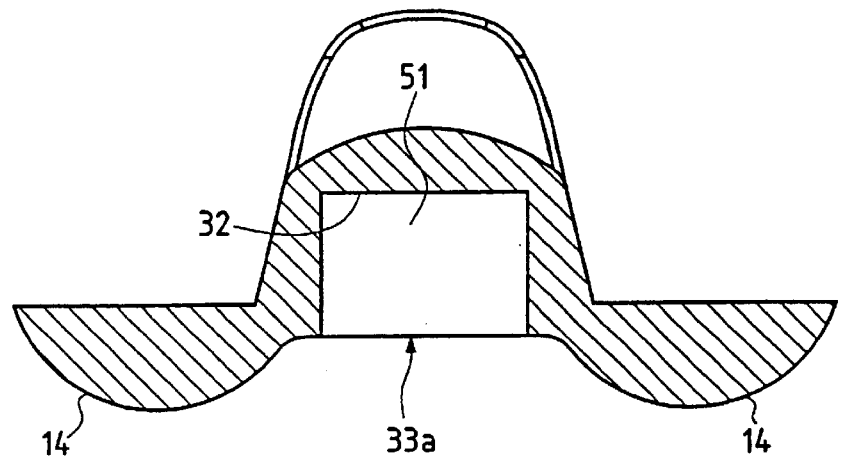
FIG. 10 is a section on line X—X of FIG. 9.

As shown in FIG. 10, the bearing surface 33a then does not have a transverse radius of curvature $R_t$ as described for the preceding embodiment, with reference to FIGS. 3 and 4.

Figure 12:
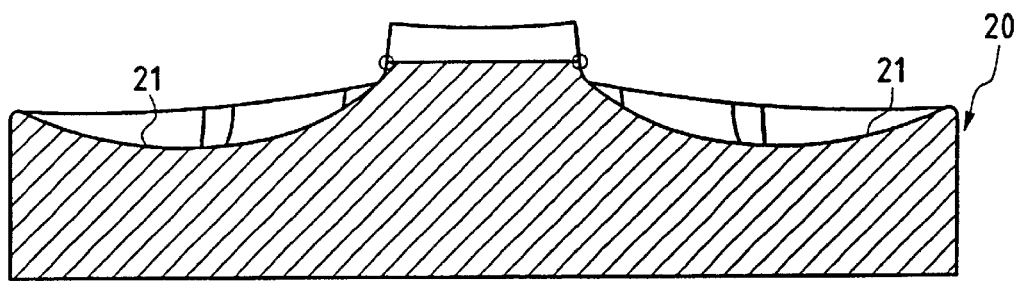
FIG. 12 is a section on line XII—XII of FIG. 11.

In this variant embodiment, the insert 20 of the prosthetic element 2 presents, starting from the projection 40, a bearing surface 41a which is formed by a concave surface 53 that is cylindrical being defined by a radius $R_{53}$ of center O and occupying an angular extent $a_{53}$. The cylindrical surface portion 53 is shown in FIG. 12 where it can be seen that in this variant, no transverse curvature is given to the ramp 41a.

As an indication, Table III below gives the ranges of numerical values for the lengths and the angular extents of the various radii of the bearing surface 33a for a set of six sizes of prosthesis.

TABLE III

|     | $R_{51}$ in mm | $R_{52}$ in mm | $a_{51}$ in ° | $a_{52}$ in ° |
|-----|-------|------|-------|-------|
| min | 15.05 | 13.3 | 87.28 | 90.76 |
| max | 20.75 | 18.3 | 89.67 | 98.47 |

By way of indication, Table IV below gives the ranges of numerical values for the radius of the ramp 41a over the same set of six sizes of prosthesis.

TABLE IV

|     | $R_{52}$ mm | $a_{53}$ in ° |
|-----|-------|--------|
| min | 15.05 | 98.46  |
| max | 20.75 | 102.6  |

Co-operation of the kind described with reference to FIGS. 1 and 7 takes place between the facing faces 33a and 41a so as to contribute to sliding and displacement in the antero-posterior plane, with any rotation then being acquired by the insert 20 pivoting relative to the base 16.

The invention is not limited to the examples described and shown, since various modifications can be applied thereto without going beyond its ambit.

What is claimed is:

1. A knee prosthesis comprising:

a U-shaped femur prosthetic element defining a housing for engaging the resectioned epiphysial portion of a femur and comprising an anterior portion defining a trochlea on its front face and a distalo-posterior portion defining two condyles between which said portion forms a block presenting, in its outer face relative to the housing, a lug connected to the trochlea and adjacent to a notch from which a convex bearing surface extends to the rearmost portion of the block; and a tibia prosthetic element comprising a base for fitting to the resectioned epiphysial portion of a tibia, and an insert mounted on the base and presenting, facing the femur prosthetic element, two glenoid cavities for co-operating with the condyles, said element including between the glenoid cavities an elevation of sagittal orientation co-operating with the front edge of said insert to define a projection for antero-posterior stabilization which is engaged in the notch in the extended position of the prosthesis and which is connected to a concave sliding ramp extending to the rear edge of the insert and co-operating with the convex portion facing it in the extended position of the prosthesis to define a gap of section that increases from the zone where the projection and the notch are in contact all the way to said rear edge, wherein the convex bearing surface is defined by:

a transverse radius of curvature $R_t$ of center O occupying an angular extent $a_t$; and a sagittal curve made up of:

à a substantially middle portion of radius $R_{35}$, of center O, and occupying an angular extent $a_{35}$;

à a front portion connecting the middle portion to the notch, having a radius $R_{34}$, a center $O_1$ situated beyond and beneath the center O relative to the anterior portion of the prosthetic element, and occupying an angular extent $a_{34}$; and à a rear portion having a radius $R_{36}$, a center $O_2$ situated beyond and beneath the center O relative to said anterior edge, and occupying an angular extent $a_{36}$.

2. A prosthesis according to claim 1, comprising a femur prosthetic element and a tibia prosthetic element whose concave sliding ramp includes:

a transverse radius of curvature $R_c$, a center O, and occupying an angular extent $a_c$; and a sagittal curve made up of:

à a front portion extending from the projection with a radius $R_{43}$, a center O, and occupying an angular extent $a_{43}$; and à a rear portion extending the front portion to the rear edge of the insert and possessing a radius $R_{44}$, a center $O_3$ situated beneath the center O, and occupying an angular extent $a_{44}$.

3. A prosthesis according to claim 1, comprising a tibia prosthetic element and a femur prosthetic element in which:

the radius $R_t$ possesses a length lying in the range 14 mm to 18 mm;

the radius $R_{34}$ possesses a length lying in the range 12.4 mm to 17 mm;

the radius $R_{35}$ possesses a length lying in the range 17.7 mm to 24.4 mm;

the radius $R_{36}$ possesses a length lying in the range 14.6 mm to 20.1 mm;

the angular extent $a_t$ occupies an angle lying in the range 70.64° to 80.87°;

the angular extent $a_{33}$ occupies an angle lying in the range 22.75° to 22.75°;

the angular extent $a_{34}$ occupies an angle of 70°; and the angular extent $a_{35}$ occupies an angle lying in the range 89.05° to 91.67°.

4. A prosthesis according to claim 1, wherein the radius $R_{35}$ is of center O known as the "reference" center, as is the radius $R_{35}$, whereas the radius $R_{34}$ is of center $O_1$ situated beyond and beneath the reference center and the radius $R_{36}$ is of center $O_2$ situated beyond and beneath the center O.

5. A prosthesis according to claim 1, comprising a femur prosthetic element and a tibia prosthetic element in which:

the radius $R_c$ possesses a length lying in the range 16 mm to 20 mm;

the radius $R_{43}$ possesses a length lying in the range 17.77 mm to 24.4 mm;

the radius $R_{44}$ possesses a length lying in the range 16.5 mm to 20.5 mm;

the angular extent $a_c$ occupies an angle lying in the range 57.42° to 64.72°;

the angular extent $a_{43}$ occupies an angle lying in the range 75.51° to 76.31°; and the angular extent $a_{44}$ occupies an angle lying in the range 35.54° to 40.02°.

6. A prosthesis according to claim 2, wherein:

the radius $R_c$ is of center O known as the "reference" center;

the radius $R_{43}$ is of center O; and the radius $R_{44}$ is of center $O_3$, situated vertically beneath the center O.

7. A prosthesis according to claim 1, wherein the convex portion of the concave femur prosthetic element and the sliding ramp of the tibia prosthetic element are formed by surface portion of pseudo-cylindrical nature, and wherein the insert is mounted on the base via a pivot.

8. A prosthesis according to claim 7, wherein the bearing surface is defined by:

a front portion having a sagittal radius of curvature $R_{51}$ of center O and occupying an angular extent $a_{51}$; and by a rear portion following the front portion and possessing a sagittal radius of curvature $R_{52}$, of center $O_4$, and occupying an angular extent $a_{52}$.

9. A prosthesis according to claim 8, wherein:

the radius $R_{51}$ possesses a length lying in the range 15.05 mm to 20.75 mm;

the radius $R_{52}$ possesses a length lying in the range 13.3 mm to 18.3 mm;

the angular extent $a_{51}$ occupies an angle lying in the range 87.28° to 89.67°; and the angular extent $a_{52}$ occupies an angle lying in the range 90.76° to 98.47°.

10. A prosthesis according to claim 7, wherein the concave sliding ramp is defined by a radius of curvature $R_{53}$ of center O occupying an angular extent $a_{53}$.

11. A prosthesis according to claim 10, wherein:

the radius $R_{53}$ possesses a length lying in the range 15.05 mm to 20.75 mm; and the angular extent $a_{53}$ occupies an angle lying in the range 98.46° to 102.6°.

* * * * *